United States Patent
Bonifacio et al.

(10) Patent No.: US 7,173,153 B2
(45) Date of Patent: Feb. 6, 2007

(54) SERTRALINE HYDROCHLORIDE FORM II AND METHODS FOR THE PREPARATION THEREOF

(75) Inventors: Fausto Bonifacio, Latina (IT); Cristina Crescenzi, Rome (IT); Maria Donnarumma, Latina (IT); Dimitri Ippoliti, Aprilia (IT)

(73) Assignee: Recordati Industria Chimica E. Farmaceutica S.p.A., Milan (IT)

( * ) Notice: Subject to any disclaimer, the term of this patent is extended or adjusted under 35 U.S.C. 154(b) by 37 days.

(21) Appl. No.: 10/891,434

(22) Filed: Jul. 14, 2004

(65) Prior Publication Data

US 2005/0032906 A1 Feb. 10, 2005

Related U.S. Application Data

(60) Provisional application No. 60/487,292, filed on Jul. 15, 2003.

(51) Int. Cl.
*C07C 209/82* (2006.01)
*C07C 209/86* (2006.01)

(52) U.S. Cl. ........................ 564/308; 564/424; 564/437

(58) Field of Classification Search ................ 564/308, 564/424, 437
See application file for complete search history.

(56) References Cited

U.S. PATENT DOCUMENTS

| 4,536,518 | A | * | 8/1985 | Welch et al. ............... 514/647 |
| 5,248,699 | A | * | 9/1993 | Sysko et al. ................ 514/647 |
| 6,495,721 | B1 | * | 12/2002 | Schwartz et al. ........... 564/308 |
| 6,500,987 | B1 | | 12/2002 | Schwartz et al. |
| 6,897,340 | B2 | * | 5/2005 | Borochovitch et al. ..... 564/428 |

FOREIGN PATENT DOCUMENTS

| CN | 1091096 B | | 9/2002 |
| WO | WE0 01/90049 | * | 11/2001 |
| WO | WO 03/093217 | | 11/2003 |

* cited by examiner

*Primary Examiner*—Thurman K. Page
*Assistant Examiner*—Chukwuma Nwaonicha
(74) *Attorney, Agent, or Firm*—Ohlandt, Greeley, Ruggiero & Perle, L.L.P.

(57) ABSTRACT

This invention relates to a method for the preparation of sertraline hydrochloride, (1S-cis)-4-(3,4-dichlorophenyl)-1,2,3,4-tetrahydro-N-methyl-1-naphtalenamine hydrochloride, in its crystalline form II.

22 Claims, No Drawings

SERTRALINE HYDROCHLORIDE FORM II AND METHODS FOR THE PREPARATION THEREOF

RELATED APPLICATIONS

This application claims priority to U.S. Provisional application No. 60/487,292 filed Jul. 15, 2003 which is incorporated herein by reference in its entirety.

BACKGROUND OF THE INVENTION

Sertraline hydrochloride is a known compound having the following structural formula:

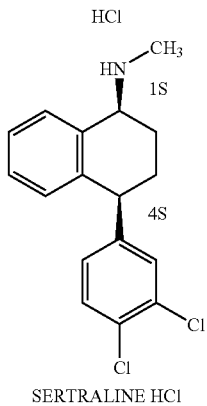

SERTRALINE HCl

Sertraline, in the form of its hydrochloride salt, is the active principle of the medicinal product known under the trademark Zoloft®, useful in the treatment of depression, obsessive-compulsive disorders, panic disorders and premature ejaculation.

Sertraline hydrochloride can exist in different crystalline forms which differ from each other in terms of stability, physical properties, spectral data and methods of preparation.

U.S. Pat. No. 4,536,518 (Pfizer Inc.) describes a synthesis of sertraline hydrochloride by treating an ethyl acetate/ether solution of the free base with gaseous hydrogen chloride. This patent does not refer to specific polymorphic crystalline forms of sertraline hydrochloride. In such case, its preparation provides for a very high diluition ratio, involving large amounts of solvent. This process also presents several problems regarding its industrial applicability, primarily due to the use of diethyl ether. Furthermore, in step c) of U.S. Pat. No. 4,536,518 hydrogenation on Pd/C is provided which may lead to dehalogenated products. As also mentioned in WO 02/102761 removing such impurities is usually quite difficult even if recrystallization of sertraline hydrochloride is carried out, so that previous recrystallization of sertraline mandelate is required, at times leading to dramatic loss of yields.

U.S. Pat. No. 5,248,699 (Pfizer Inc.) discloses 5 polymorphic forms of sertraline hydrochloride (I, II, III, IV and V), which can be characterized by single crystal x-ray analysis, powder x-ray diffraction, infra-red spectroscopy and differential scanning calorimetry.

According to U.S. Pat. No. 5,248,699, sertraline hydrochloride produced by the method of U.S. Pat. No. 4,536,518 has a crystalline form corresponding to form II.

U.S. Pat. No. 5,248,699 also reports that form II is produced by rapid crystallization of sertraline hydrochloride from an organic solvent, including isopropyl alcohol, hexane, acetone, methyl isobutyl ketone, glacial acetic acid and ethyl acetate. The preferential formation of form I, II or IV in an acidic solution of an organic solvent such as those listed above depends on the rapidity of crystallization, but crystallization kinetics and cooling time are not easily controlled in an industrial plant.

U.S. Pat. No. 5,248,699 also discloses methods for preparing sertraline hydrochloride form II from sertraline chloride form V or VI, such as granulation (in methanol or ethanol), reslurry in an organic solvent and crystallization in DMF or cyclohexanol.

U.S. Pat. No. 6,495,721 (Teva Pharm. Ind.) describes processes for making sertraline chloride form II comprising the steps of dissolving sertraline base or its mandelate salt in an organic solvent, selected from the group consisting of ethyl acetate, acetone, hexane, t-butyl-methyl ether, isopropyl alcohol, n-butanol, t-butanol, isobutanol, and cyclohexane, to form a solution; adding hydrogen chloride to the solution; heating the solution for a time sufficient to induce the formation of sertraline hydrochloride; and isolating sertraline hydrochloride form II.

Some of the examples of methods for the preparation of sertraline hydrochloride as described in U.S. Pat. No. 6,495,721 were reproduced for experimental purposes, particularly those according to examples 4 to 10 thereof. By following said examples, it was found that sertraline hydrochloride form II could not be obtained, at least in a reproducible manner and in sufficient yield, since in some cases form I or at most a mixture of form I and form II was actually obtained.

In particular, sertraline hydrochloride form I was obtained by following examples 4, 6, 7, 9, 10

Form II thereof was only obtained from examples 5 and 8 but remarkably mixed with form I, in a form II 75% yield and 60% yield, respectively.

Therefore, it could be concluded that the above teachings taken from U.S. Pat. No. 6,495,721 do not allow to obtain sertraline chloride form II on a reliable industrial scale production, due to the poor reproducibility of the preparation methods thereof and in any case to insufficient yields.

A purpose of the instant invention is to provide a suitable method for selectively preparing pure sertraline hydrochloride form II in high yield and in a reproducible manner on an industrial scale, by thus solving the problems involved in working the above prior art.

DESCRIPTION OF THE INVENTION

The invention relates to a method of selectively preparing pure sertraline hydrochloride form II in high yield and in a repeatable and convenient manner on an industrial scale, comprising the step of crystallizing sertraline hydrochloride in an acidic solution of an organic solvent selected among the following: n-propanol, n-pentanol, n-hexanol, n-heptanol, n-octanol, acetonitrile, 1-methyl-2-piperidone, and mixtures thereof.

The critical crystallization step according to the invention can be carried out by starting either from sertraline base or from its citrate salt, as it will be apparent in the following.

In a preferred embodiment, the method of the invention comprises the following steps:

a) Sertraline, as base or citrate salt, is dissolved in said solvent selected from the group consisting of n-propanol, n-pentanol, n-hexanol, n-heptanol, n-octanol, acetonitrile, 1-methyl-2-piperidone and mixtures thereof.

b) The solution of sertraline in the said solvent is kept at room temperature, or heated to a maximum temperature corresponding to the reflux temperature of the said solvent.

c) Hydrogen chloride (gaseous hydrogen chloride, or aqueous hydrogen chloride or a solution of hydrogen chloride with one of the said organic solvent) is mixed with the said solution of sertraline until pH=0 is reached.

d) The mixture is stirred for about one hour and then, if previously heated, cooled to room temperature.

e) Sertraline hydrochloride form II is isolated by filtration.

In one embodiment of the invention, in the said step b) the solution is heated at a specific temperature selected in the range between room temperature and the solvent reflux temperature.

In another embodiment of the invention, in the said step b) the solution is heated to the solvent reflux temperature.

In one embodiment of the invention, in said step c) hydrogen chloride as aqueous hydrogen chloride or gaseous hydrogen chloride is added to the said solvent to form a corresponding hydrogen chloride solution, and a solution of sertraline in said solvent is then added, preferably dropwise, to the hydrogen chloride solution thus obtained.

In another embodiment, in said step c) hydrogen chloride is added to the said solution of sertraline as gaseous hydrogen chloride.

In a further embodiment, in said step c) hydrogen chloride is added to the said solution of sertraline as aqueous hydrogen chloride.

Sertraline hydrochloride form II thus obtained has been characterized by means of IR and X-ray crystallographic analysis. According to the method of the invention, specific form II has been found to be selectively obtained in a very high yield (95%) and in a repeatable manner.

The use of sertraline citrate according to the method of the invention provides further advantages: in fact, in step c) of U.S. Pat. No. 4,536,518 mentioned above hydrogenation on Pd/C is provided which leads to dehalogenated by-products. As also mentioned in WO 02/102761 removing such impurities is usually quite difficult even if recrystallization of sertraline hydrochloride is carried out, so that previous recrystallization of sertraline mandelate is required, with at times dramatic loss of yields.

According to a further aspect of the present invention, it has been surprisingly found that conversion of sertraline base containing dehalogenated impurities to its citrate salt occurs in high yields and leads to sertraline citrate endowed with high purity.

When the method of the invention is subsequently performed on the thus obtained sertraline citrate, it leads to sertraline hydrochloride form II containing less than 0.1% of dehalogenated impurities.

EXAMPLES

In order to further illustrate the present invention, examples are described in the following without limiting the scope of the invention.

It is made clear that Example 1 relates to a prior art preparation of sertraline base from sertraline mandelate. Sertraline mandelate mentioned in example 1 can be prepared, for instance, according to U.S. Pat. No. 5,248,699.

Example 15 is a comparative example taken from the prior art of U.S. Pat. No. 6,495,721.

Examples 16 to 19 relate to embodiments of the invention using sertraline citrate.

Example 1

150 g of sertraline mandelate, 900 ml of water, 66 ml of 30% sodium hydroxide and 450 ml of toluene are fed into a 3-neck 2 litre flask equipped with mechanical stirrer, thermometer and dropping funnel.

The mixture is heated to 70° C. and maintained for 30 minutes under stirring until two clear emulsion-free phases are obtained.

The phases are decanted and separated. The aqueous phase is extracted with 300 ml toluene and the pooled organic phases are washed with 2×300 ml of demineralised water.

The organic phase is concentrated under vacuum to obtain sertraline base as an oil (103 g).

Example 2

A solution of 50 g free sertraline base in 100 ml of n-propanol was added dropwise over a period of about 30 minutes at ambient temperature onto 100 ml of n-propanol containing 13 ml of 37% aqueous hydrochloric acid. About 10 minutes after the end of the addition a white crystalline solid starts to form. Stirring is maintained for 1 hour then the solid is filtered and washed. It is dried under vacuum. 47.5 g of sertraline hydrochloride form II are obtained in a 85% yield.

Example 3

A solution of 51.4 g free sertraline base in 100 ml of n-pentanol was added dropwise over a period of about 30 minutes at room temperature onto 100 ml of n-pentanol containing 13 ml of 37% aqueous hydrochloric acid. About ¾ of the way through the addition a white crystalline solid starts to form. Stirring is maintained for 1 hour then the solid is filtered and washed. It is dried under vacuum. 50 g of sertraline hydrochloride form II are obtained in a yield of 87%.

Example 4

A solution of 50.8 g free sertraline base in 100 ml of n-hexanol was added dropwise over a period of about 30 minutes at room temperature onto 100 ml of n-hexanol containing 14 ml of 37% aqueous hydrochloric acid. About ¾ of the way through the addition a white crystalline solid starts to form. Stirring is maintained for 1 hour then the solid is filtered and washed. It is dried under vacuum. 49.5 g of sertraline hydrochloride form II are obtained in a yield of 87%.

Example 5

A solution of 50.9 g free sertraline base in 100 ml of n-heptanol was added dropwise over a period of about 30 minutes at room temperature onto 100 ml of n-heptanol containing 14 ml of 37% aqueous hydrochloric acid. At the end of the addition a white crystalline solid starts to form. Stirring is maintained for 1 hour then the solid is filtered and washed. It is dried under vacuum. 50.1 g of sertraline hydrochloride form II are obtained in a yield of 88%.

Example 6

A solution of 53 g free sertraline base in 100 ml of n-octanol was added dropwise over a period of about 30 minutes at room temperature onto 100 ml of n-octanol containing 15 ml of 37% aqueous hydrochloric acid. About half way through the addition a white crystalline solid starts to form. Stirring is maintained for 1 hour then the solid is filtered and washed. It is dried under vacuum. 53.4 g of sertraline hydrochloride form II are obtained with a yield of 90%.

Example 7

A solution of 15 ml of aqueous hydrochloric acid 37% in 100 ml of n-propanol was heated at 45° C. and a solution of 50 g free sertraline base in 100 ml of n-propanol was added dropwise over a period of about 30 minutes. About 20 minutes after the end of the addition a white crystalline solid starts to form. The suspension is stirred for 1 hour at 45° C., then cooled to room temperature within 1 hour. The solid is filtered, washed and dried under vacuum. 49.2 g of sertraline hydrochloride form II are obtained in a 88% yield.

Example 8

6.1 g of HCl gas were bubbled into 100 ml of n-propanol and a solution of 50 g free sertraline base dissolved in 100 ml of n-propanol was added dropwise onto the mixture obtained.

During the addition the temperature rises to 30° C. About half way through the addition a crystalline solid starts to precipitate. Stirring is maintained for 1 hour then the solid is filtered and washed. It is dried under vacuum. 53.8 g of sertraline hydrochloride form II are obtained with a yield of 96%.

Example 9

4.7 g of HCl gas were bubbled into 80 ml of n-pentanol and a solution of 40 g free sertraline base dissolved in 80 ml of n-pentanol was added dropwise onto the mixture obtained.

A solid gel immediately starts to precipitate which rapidly fluidifies and transforms into a crystalline solid. During the addition the temperature rises to 35° C. Stirring is maintained for 1 hour, then the solid is filtered and washed. It is dried under vacuum. 42.5 g of sertraline hydrochloride form II are obtained in a yield of 95%.

Example 10

5.9 g of HCl gas were bubbled into 150 ml of n-hexanol and a solution of 50 g free sertraline base dissolved in 150 ml of n-hexanol was added dropwise onto the mixture obtained.

About half way through the addition a solid gel starts to precipitate which rapidly fluidifies and transforms into a crystalline solid. During the addition the temperature rises to 40° C. Stirring is maintained for 1 hour then the solid is filtered and washed. It is dried under vacuum. 52 g of sertraline hydrochloride form II are obtained with a yield of 93%.

Example 11

6.3 g of HCl gas were bubbled into 150 ml of n-heptanol and a solution of 50.3 g free sertraline base dissolved in 150 ml of n-heptanol was added dropwise onto the mixture obtained.

A solid gel immediately starts to precipitate which rapidly fluidifies and transforms into a crystalline solid. During the addition the temperature rises to 35° C. Stirring is maintained for 1 hour then the solid is filtered and washed. It is dried under vacuum. 52 g of sertraline hydrochloride form II are obtained with a yield of 93%.

Example 12

6.5 g of HCl gas were bubbled into 100 ml of n-octanol and a solution of 50 g free sertraline base dissolved in 100 ml of n-octanol was added dropwise onto the mixture obtained.

At the end of the addition a solid gel precipitates which fluidifies and transforms into a crystalline solid. Stirring is maintained for 1 hour then the solid is filtered and washed. It is dried under vacuum. 53 g of sertraline hydrochloride form II are obtained with a yield of 95%.

Example 13

HCl gas was bubbled into a solution of sertraline base (40 g) in n-propanol (320 ml). The temperature reaches about 40° C. A stirrable solid gel is formed. HCl addition continues until pH=0.5. Stirring is maintained for 1 hour. The solid was filtered, washed with n-propanol (2×15 ml) and dried at 80° C. for 24 hours. 40 g of sertraline hydrochloride form II are obtained. (Yield 90%).

Example 14

6.1 g of HCl gas were bubbled into 100 ml of acetonitrile and a solution of 50 g free sertraline base dissolved in 100 ml of acetonitrile was added dropwise onto the mixture obtained.

A crystalline solid immediately precipitates. Stirring is maintained for 1 hour then the solid is filtered, washed and dried under vacuum. 53 g of sertraline hydrochloride form II are obtained with a yield of 95%.

Comparative Example 15 (Taken from U.S. Pat. No. 6,495,721, Example 5)

HCl gas was bubbled into a solution of sertraline base (33 g) in n-butanol (264 ml). The temperature reaches about 45° C. A solid gel forms which is difficult to stir. HCl addition continues until pH=0.5. Stirring is maintained for 2.5 hours to allow transformation of the solid gel to a crystalline solid. The solid was filtered, washed with n-butanol (2×10 ml) and dried at 80° C. for 24 hours. 28 g of sertraline hydrochloride form II impure with Form I are obtained. (Yield 75%).

Example 16

53.8 g of citric acid and 160 ml of n-propanol are fed into a 1 litre flask. The mixture is heated to T=40° C. and a solution of 80 g of free sertraline base dissolved in 320 ml isopropanol is added to it dropwise.

A white solid precipitates very slowly ¾ of the way through the addition. Stirring is maintained for 1 hour. The solid is cooled to T=0–5° C. and maintained under stirring for 1 hour. It is filtered and washed with 80 ml of isopropanol. It is dried at 50° C. for 16 hours. 125 g of sertraline citrate (yield 96%) are obtained.

Example 17

30.1 g of citric acid, 300 ml of ethyl acetate and 5 ml of water are fed into a 1 litre flask. The mixture is heated to T=60° C. and a solution of 50.5 g of free sertraline base dissolved in 100 ml ethyl acetate is added to it dropwise.

A white solid precipitates very slowly ¾ of the way through the addition. The solid is cooled to T=0–5° C. and maintained under stirring for 1 hour. It is filtered and washed with 50 ml of ethyl acetate. It is dried at 50° C. for 16 hours. 79.8 g of sertraline citrate (yield 97%) are obtained.

Example 18

60 g of sertraline citrate are dissolved in 240 ml of n-propanol at T=70° C. The mixture is acidified with 37% aqueous hydrochloric acid to pH=0.

A triggering amount of 1 g of sertraline hydrochloride form II is added to the solution. It is allowed to spontaneously reach ambient temperature. A crystalline solid precipitates which is maintained under stirring for 1 hour, isolated by filtration and dried under vacuum. 37 g of sertraline hydrochloride Form II (yield 90%) are obtained.

Example 19

A suspension of 40 g of sertraline citrate in 240 ml of acetonitrile is treated with a solution of HCl gas (5 g) in acetonitrile (100 ml) at ambient temperature. The appearance of the solid present in suspension changes rapidly.

Stirring is maintained for 1 hour. The solid is filtered, washed and dried under vacuum.

26 g of sertraline hydrochloride form II (yield 95%) are obtained.

The above detailed description of the invention shows that the purpose as set forth above of providing a selective method of obtaining pure sertraline hydrochloride form II in high yield and with a reproducible process so as to allow to perform it on an industrial scale is successfully achieved.

We claim:

1. A method of selectively preparing pure sertraline hydrochloride form II, comprising the step of crystallizing sertraline hydrochloride in an acidic solution of an organic solvent selected from the group consisting of acetonitrile, 1-methyl-2-piperidone, and mixtures thereof.

2. The method according to claim 1, characterized in that it is carried out by forming sertraline hydrochloride from a solution of either sertraline base or the salt sertraline citrate in said solvent.

3. The method according to claim 1, characterized in that it further comprises the following steps:
   a) dissolving sertraline base or citrate salt in said solvent selected from the group consisting of acetonitrile, 1-mexhyl-2-piperidone and mixtures thereof;
   b) heating the solution of sertraline in said solvent at a temperature between about room temperature and the reflux temperature of said solvent;
   c) mixing hydrogen chloride with said solution of sertraline until pH=0 is reached;
   d) stirring the mixture for a predetermined time and then cooling to room temperature; and
   e) separating sertraline hydrochloride form II by filtration.

4. The method according to claim 3, characterized in that in step b) the solution is heated at any temperature in the range below the solvent reflux temperature to the solvent reflux temperature.

5. The method according to claim 3, characterized in that in step b) said solution is heated at the reflux temperature of said solvent.

6. The method according to claim 3, further characterized in that in step C) hydrogen chloride as aqueous hydrogen chloride or gaseous hydrogen chloride is added to said solvent to form a corresponding hydrogen chloride solution, and a solution of sertraline in said solvent is then added to the hydrogen chloride solution thus obtained.

7. The method according to claim 3, characterized in that in said step c), the hydrogen chloride is added to said solution of sertraline as gaseous hydrogen chloride.

8. The method according to claim 3, characterized in that in step c), the hydrogen chloride is added to said solution of sertraline as aqueous hydrogen chloride.

9. The method according to claim 3, characterized in that in step d) the predetermined time is for about one hour.

10. A method of selectively preparing pure sertraline hydrochloride form II, comprising the steps of:
    a) dissolving sertraline base or citrate salt in a solvent selected from the group consisting of n-pentanol n-hexanol, n-heptanol, n-octanol, acetonitrile, 1-methyl-2-piperidone and mixtures thereof;
    b) heating the solution of sertraline in said solvent at a temperature between about room temperature and the reflux temperature of said solvent;
    c) mixing aqueous hydrogen chloride with said solution of sertraline until pH=0 is reached;
    d) stirring the mixture for a predetermined time and then cooling to room temperature; and
    e) separating sertraline hydrochloride form II by filtration.

11. The method according to claim 10, characterized in that it is carried out by forming sertraline hydrochloride from a solution of either sertraline base or the salt sertraline citrate in said solvent.

12. The method according to claim 10, characterized in that in step b) the solution is heated at any temperature in the range below the solvent reflux temperature to the solvent reflux temperature.

13. The method according to claim 10, characterized in that in step b) said solution is heated at the reflux temperature of said solvent.

14. The method according to claim 10, further characterized in that in step c) the aqueous hydrogen chloride is added to said solvent to form a corresponding hydrogen chloride solution, and a solution of sertraline in said solvent is then added to the hydrogen chloride solution thus obtained.

15. The method according to claim 10, characterized in that in step d) the predetermined time is for about one hour.

16. The method according to claim 10 characterized in that said solvent is n-pronanol.

17. The method according to claim 10 characterized in that said solvent is n-pentanol.

18. The method according to claim 10 characterized in that said solvent is n-hexanol.

19. The method according to claim 10 characterized in that said solvent is n-heptanol.

20. The method according to claim 10 characterized in that said solvent is n-octanol.

21. The method according to claim 10 characterized in that said solvent is acetonitrile.

22. The method according to claim 10 characterized in that said solvent is 1-methyl-2-piperidone.

* * * * *